United States Patent [19]

Hutchings

[11] Patent Number: 4,641,518
[45] Date of Patent: Feb. 10, 1987

[54] PROCESS FOR THE NON-DESTRUCTIVE INSPECTION OF SURFACE DEFECTS

[75] Inventor: David J. Hutchings, Wiesloch, Fed. Rep. of Germany

[73] Assignee: Brent Chemicals International PLC, Buckinghamshire, Great Britain

[21] Appl. No.: 762,065

[22] PCT Filed: Nov. 16, 1984

[86] PCT No.: PCT/EP84/00362
§ 371 Date: Jul. 25, 1985
§ 102(e) Date: Jul. 25, 1985

[87] PCT Pub. No.: WO85/02464
PCT Pub. Date: Jun. 6, 1985

[30] Foreign Application Priority Data

Nov. 26, 1983 [DE] Fed. Rep. of Germany ....... 3342855

[51] Int. Cl.$^4$ ............................................. G01N 21/91
[52] U.S. Cl. ................................. 73/104; 252/301.19; 252/408.1; 250/302
[58] Field of Search ......................... 252/408.1, 301.19; 73/104, 40.7; 250/302; 436/3, 5

[56] References Cited

U.S. PATENT DOCUMENTS

| | | |
|---|---|---|
| 3,108,187 | 10/1963 | Thornbury . |
| 3,506,827 | 4/1970 | Alburger ...................... 252/301.19 X |
| 3,557,015 | 1/1971 | Alburger .......................... 252/301.19 |
| 3,564,249 | 2/1971 | Molina ............................... 73/104 X |
| 3,679,598 | 7/1972 | Alburger ......................... 252/301.19 |
| 3,928,046 | 12/1975 | Alburger . |
| 4,377,492 | 3/1983 | Jones .............................. 252/301.19 |

FOREIGN PATENT DOCUMENTS 1135408 12/1978 United Kingdom ................. 73/104

Primary Examiner—Jerry W. Myracle
Assistant Examiner—Tom Noland
Attorney, Agent, or Firm—Antonelli, Terry & Wands

[57] ABSTRACT

In a process for the non-destructive inspection of surface defects, initially a solution with one or more dyes substantially having no emission under UV-light are applied and excess solution is removed after the dye has penetrated the surface defects, the surface is then covered with a developer leaving behind an absorbent coating with a high-contrast in daylight and which exclusively has one or more optical brighteners in a proportion between 0.02 and 2.0% by weight. The coating absorbs the dye from the surface defects, which appear as black traces on the coating under UV-light.

17 Claims, No Drawings

PROCESS FOR THE NON-DESTRUCTIVE INSPECTION OF SURFACE DEFECTS

BACKGROUND OF THE INVENTION

The present invention relates to a process for the non-destructive inspection of surface defects, in that initially a solution with one or more dyes essentially having no emission under UV-light is applied and excess solution is removed after the dye has penetrated the surface defects and then the surface is covered with a developer leaving behind an absorbent coating and which contains at least one fluorescent component, the surface defects being revealed under UV-light as blackened portions within the light-emitting ambient.

For the non-destructive inspection or detection of surface defects, particularly on metal surfaces, the so-called red/white process is frequently used and consists of applying a solution with a dye having a high contrast in daylight to the surface, so that solution and dye can penetrate the surface defects. The excess solution is then removed from the surface, so that no dye residues are left behind. A coating is then applied, which leaves behind a background contrasting with the dye. For example, it can be a solvent with dispersed talc. After drying the coating, and surface defects are revealed by the coloring of the absorbent talc with the dye left behind in the surface defects.

A supplement to this process has been proposed for showing very small surface defects, such as cracks and the like (U.S. Pat. No. 3,564,249). In this process, following the wiping off of the dye applied, a developer is applied, which once again leaves behind a contrasting, e.g. approximately white and absorbent coating. This developer additionally contains a fluorescent component, which emits under UV-light. The absorbent component of the coating, which can also consist of talc, once again removes the dye from the surface defects. A complementary color is formed at the corresponding points from the dye and the fluorescent component and appears as a blackened portion under UV-light. These blackened portions can be detected clearly and in a sharply defined manner even when the red/white process leaves behind no or only unclear colorings. It is also pointed out that it need not be exclusively a red dye and also dyes in the blue range can be considered.

The known developer should contain approximately 1.5% of the essential component Fluoral 7 GA (product of General Aniline and Film Corporation). It is also proposed to add 3.2% of an optical brightener, in addition to the fluorescent dye.

Fluoral 7 GA and similar fluorescent dyes give the coating a striking yellow coloring, which impairs contrast in daylight. The problem to be solved by the present invention is to permit a better contrast within the coating.

SUMMARY OF THE INVENTION

On the basis of the aforementioned process, this problem is solved in that the fluorescent component is solely constituted by one or more optical brighteners in a proportion between 0.02 and 2.0% by weight of the total weight of the developer.

Practical tests with the developer having a composition according to the invention and which contains as the fluorescent component solely an optical brightener which is invisible in daylight in a much larger proportion compared with the Prior Art, have shown that the coating provides a high-contrast background both for the red/white process and for the UV-process, so that surface defects in daylight are made readily apparent by the red coloring and in UV-light by the blackening. In addition, fluorescent dyes are relatively expensive, whereas optical brighteners are used on an industrial scale in washing and bleaching agents and are consequently inexpensive. Thus, the invention not only provides an agent with improved use characteristics and consequently a more precise inspection process, but in addition the developer can also be produced less expensively.

DESCRIPTION OF THE PREFERRED EMBODIMENTS

According to a preferred embodiment, the optical brightener is added to the developer in a proportion of 0.05 to 0.5% by weight. This makes it clear how small the added optical brightener quantity can be without having to accept losses in the precision of the inspection process.

The developer may comprise 70 to 95% by weight solvent, 5 to 30% by weight talc, 0 to 1.0% by weight wetting agent and 0.05 to 0.5% by weight optical brightener.

According to an embodiment, the developer consists of 88.8% by weight solvent, 11.0% by weight talc, 0.1% by weight wetting agent and 0.1% by weight optical brightener.

All industrially available optical brighteners can be used for the process according to the invention. These optical brighteners absorb long-wave UV-light in the range 350 to 390 nm and emit light in the visible range between 420 and 500 nm. A specific example is 7-Diethylamino-4-methyl-kumarin.

The process according to the invention can not only be used for the initial inspection of surfaces, but also as a checking process for the aforementioned red/white or UV-processes. In this process, initially a solution with one or more dyes having substantially no light emission under UV-light are applied, excess solution is removed after the dye has penetrated into the surface defects and then an absorbent coating having a contrast under daylight is applied. It is then possible to detect the areas of the coating which have become colored by the dye under daylight or UV-light. Sources of error not infrequently occur in such processes because colorings with only a limited contrast are obtained and are then difficult to interpret. There can also be discontinuities in the coloring, in that e.g. microflaws on the coating do not appear as a continuous line and instead give individual punctiform coloring zones, so that in conjunction with other surface defects also leading to punctiform or zonal colorings, it is not possible to conclude that there is a crack.

According to a preferred embodiment when there are uncertainties or lack of clarity regarding the representation of surface defects by one of the known processes, it is proposed that the area surrounding the colored zones providing dubious information are removed from the coating, preferably by wiping off and is followed by the application of the developer according to the invention, which contains as the sole fluorescent component at least one optical brightener in a proportion between 0.02 and 2.0% by weight of the total developer weight.

This process makes it possible to check in a planned manner areas providing doubtful information and resulting from the red/white or UV-process. It has been found that after wiping off the coating from the first process, there is still an adequate dye reserve in the surface defects to ensure an adequate penetration of the optical brightener into the coating, so that then there is a completely satisfactory blackening action under UV-light, which provides reliable information on the nature of the surface defect.

Isopropanol can be used as a solvent for the developer according to the invention. It is also possible to use 1,1,1-Trichloroethane and mixtures of solvents. A wetting agent which has proved satisfactory is Ethoduomeen T 13 (Akzo product and trademark) and this is based on tall oil. Not only talc can be used as the absorbent, contrast-giving component of the coating and it is also possible to use other inert powders, such as amorphous silicon dioxide or magnesium carbonate, which have given good results.

I claim:

1. A process for the non-destructive inspection of surface defects, where initially a solution with one or more dyes having substantially no emission under UV-light is applied to the surface being inspected and the excess solution is removed after the dye has penetrated the surface defects of the surface being inspected, the surface is then coated with an absorben fluorescent developer leaving behind an absorbent fluorescent developer coating that in daylight is in high contrast to the color to the color of the dye initially applied and contains at least one fluorescent component such that the absorbent fluorescent developer coating fluoresces under UV-light, so that when UV-light is applied to said surface being inspected its surface defects appear thereunder as blackened portions within the lightemitting ambient resulting from fluorescing by the absorbent fluorescent developer coating, the improvement being that the absorbent fluorescent developer used has its at least one fluuoescent component exclusively constituted by at least one optical brightener in a proportion between 0.02 and 2.0% by weight of the total absorbent fluorescent developer weight.

2. Process according to claim 1, characterized in that, optical brightener is added in a proportion of 0.05 to 0.5% by weight to the total absorbent flourescent developer weight.

3. Process according to claims 1 or 2, characterized in that, the absorbent flourescent developer comprises 70 to 95% by weight solvent, 5 to 30% by weight talc, 0 to 1.0% by weight wetting agent and 0.05 to 0.5% by weight optical brightener.

4. Process according to claim 3 wherein between the steps of removing the excess solution and applying the absorbent fluorescent developer, an absorbent coating having a color that in daylight is in high contrast to the color of the dye initially applied is applied, dye colored areas of the coating are examined and any areas of doubtful informative character surrounding the colored areas are removed.

5. Process according to claim 4, wherein the dye colored areas of the coating are examined under daylight.

6. Process according to claim 4, wherein the dye colored areas of the coating are examined under UV-light.

7. Process according to claim 4, wherein the areas of doubtful informative character surrounding the colored areas are removed by wiping.

8. Process according to claim 4, wherein after the absorbent fluorescent developer is applied, the surface is inspected under UV-light.

9. Process according to claim 3, wherein the solvent is at least one material selected from the group consisting of isopropanol and 1,1,1-Trichloroethane.

10. Process according to claim 3, wherein the wetting agent is based on tall oil.

11. Process according to claims 1 or 2 wherein between the steps of removing the excess solution and applying the absorbent fluorescent developer, an absorbent coating having a color that in daylight is in high contrast to the color of the dye initially applied is applied, dye colored areas of the coating are examined and any areas of doubtful informative character surrounding the colored areas are removed.

12. Process according to claim 11, wherein the dye colored areas of the coating are examined under daylight.

13. Process according to claim 11, wherein the dye colored areas of the coating are examined under UV-light.

14. Process according to claim 11, wherein the areas of doubtful informative character surrounding the colored areas are removed by wiping.

15. Process according to claim 11, wherein after the absorbent fluorescent developer is applied, the surface is inspected under UV-light.

16. Process according to claim 1, wherein the at least one optical brightener is 7-Diethylamino-4-Methyl-Kumarin.

17. Process according to claim 1, wherein the absorbent fluorescent developer contains an absorbent selected from the group consisting of talc, silicon dioxide and magnesium carbonate.

* * * * *